United States Patent

Ohnota et al.

Patent Number: 5,342,850
Date of Patent: Aug. 30, 1994

[54] THIAZOLIDINE-2,4-DIONE DERIVATIVES, THEIR SALTS AND THEIR PREPARATION PROCESSES

[75] Inventors: Michiro Ohnota, Nogi; Kyuya Okamura; Yoshihiro Hirata, both of Ohmiya; Koji Murakami, Nogi; Mitsuo Ohashi, Ohmiya, all of Japan

[73] Assignee: Kyorin Pharmaceutical Co., Ltd., Tokyo, Japan

[21] Appl. No.: 934,519

[22] PCT Filed: Feb. 24, 1992

[86] PCT No.: PCT/JP92/00189
§ 371 Date: Oct. 22, 1992
§ 102(e) Date: Oct. 22, 1992

[87] PCT Pub. No.: WO92/14719
PCT Pub. Date: Sep. 3, 1992

[30] Foreign Application Priority Data

Feb. 25, 1991 [JP] Japan .................. 3-053275
Feb. 21, 1992 [JP] Japan .................. 4-072496

[51] Int. Cl.$^5$ .................. C07D 277/34; A01K 31/425
[52] U.S. Cl. .................. 514/369; 514/342; 546/280; 548/183
[58] Field of Search .................. 548/183; 546/280; 514/369, 342

[56] References Cited

U.S. PATENT DOCUMENTS 5,002,953  3/1991  Hindley .................. 514/275

FOREIGN PATENT DOCUMENTS 55-22636  2/1980  Japan .
57-28073  2/1982  Japan .
59-137474  8/1984  Japan .

Primary Examiner—Robert Gerstl
Attorney, Agent, or Firm—Oblon, Spivak, McClelland, Maier & Neustadt

[57] ABSTRACT

The present invention provides novel thiazolidine-2,4-dione derivatives possessing blood sugar-lowering action and aldose reductase-inhibitory action, their salts, their preparative processes and drugs containing them, and relates to thiazolidine-2,4-dione derivatives represented by a general formula (1)

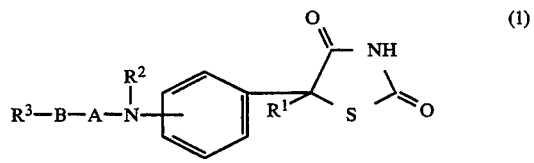

(1)

[wherein $R^1$ and $R^2$ denote identically or differently hydrogen atoms or lower alkyl groups, $R^3$ denotes a phenyl group, naphthyl group, benzoyl group or 5-membered or 6-membered heteroring and its benzene-condensed ring, which may have one or more substituents, A denotes a carbonyl group, sulfonyl group or bonding hand, and B denotes a lower alkylene, lower alkenylene or bonding hand], or their salts, or thiazolidine-2,4-dione derivatives represented by a general formula (2)

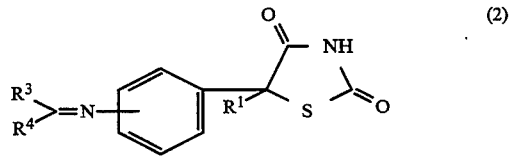

(2)

[wherein $R^4$ denotes a hydrogen atom or lower alkyl group, and $R^1$ and $R^3$ are same as above ], or their salts.

14 Claims, No Drawings

THIAZOLIDINE-2,4-DIONE DERIVATIVES, THEIR SALTS AND THEIR PREPARATION PROCESSES

TECHNICAL FIELD

The present invention relates to novel thiazolidine-2,4-dione derivatives prossesing blood sugar-lowering action and aldose reductase-inhibitory action, their salts, their preparation processes and a drug containing them. Background techniques As therapeutic agents for diabetes, various biguanide type and sulfonylurea type compounds have been used so far. However, the biguanide type compounds cause the lactic acid acidosis and the sulfonylurea type compounds cause serious hypoglycemia posing a problem on their adverse effect, thus the advent of therapeutic agent for diabetes without such defect is desired.

On the other hand, it has been made clear that the aldose reductase takes part in the crisis of diabetic complication (J. H. Kinoshita et al, J. Am. Med. Assoc. 246, 257 (1981)) . Thus inhibition of the aldose reductase may bring prevention and therapy of diseases occurring as diabetic complications.

Compounds possessing blood sugar-lowering action and compounds possessing inhibitory action of aldose reductase have been extensively searched each separately.

For example, as the aldose reductase-inhibitory agents, particular thiazolidine-2,4-dione derivatives are already publicly known (Japanese Unexamined Patent Publication No. Sho 57-28073, Chem. Pharm. Bull. 30(10) , 3601, (1982)). Namely, it is publicly known that 5-phenylthiazolidine-2,4-dione derivatives represented by a general formula

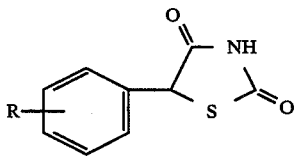

[wherein R denotes a hydrogen atom, lower alkyl group, hydroxyl group, alkoxy group, nitro group, amino group, lower acylamino group, halogen or trifluoromethyl group], have aldose reductase-inhibitory action.

However, thiazolidine-2,4-dione derivatives of the present invention represented by a general formula (1)

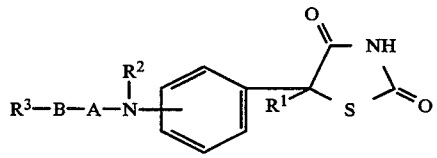

[wherein $R^1$ and $R^2$ each independently represent hydrogen atoms or lower alkyl groups, $R^3$ denotes a phenyl group, naphthyl group, benzoyl group or 5-membered or 6-membered heteroring and its benzene-condensed ring, which may have one or more substituents, A denotes a carbonyl group, sulfonyl group or bonding hand, and B denotes a lower alkylene, lower alkenylene or bonding hand ], or their salts and thiazolidine-2,4-dione derivatives of the present invention represented by a general formula (2)

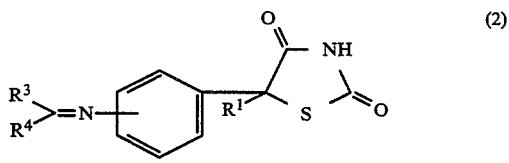

[wherein $R^4$ denotes a hydrogen atom or lower alkyl group, and $R^1$ and $R^3$ are same as above ], were not known at all, and also it could not be anticipated that thiazolidine-2,4-dione derivatives of the present invention had superior blood sugar-lowering action together with strong aldose reductase-inhibitory action.

The purpose of the present invention is to provide compounds having superior blood sugar-lowering action and simultaneously strong aldose reductase-inhibitory action and being useful as effective and highly-safe drugs capable of preventing and treating diabetes and complication thereof.

Disclosure of the invention

As a result of diligent studies for solving such problems, the inventors have found that thiazolidine-2,4-dione derivatives represented by the general formula (1)

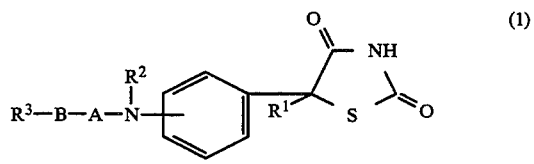

[wherein $R^1$ and $R^2$ each independently represent hydrogen atoms or lower alkyl groups, $R^3$ denotes a phenyl group, naphthyl group, benzoyl group or 5-membered or 6-membered heteroring and its benzene-condensed ring, which may have one or more substituents, A denotes a carbonyl group, sulfonyl group or bonding hand, and B denotes a lower alkylene, lower alkenylene or bonding hand], or their salts and thiazolidine-2,4-dione derivatives represented by the general formula (2)

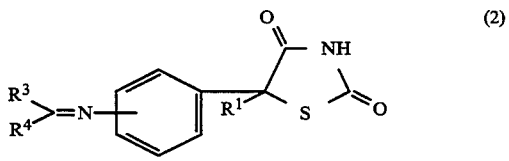

[wherein $R^4$ denotes a hydrogen atom or lower alkyl group, and $R^1$ and $R^3$ are same as above], or their salts have superior blood sugar-lowering action together with aldose reductase-inhibitory action, leading to the completion of the present invention.

For the "lower alkyl" shown in the present invention, straight chain or branched ones with carbon atoms of 1 to 6 such as methyl, ethyl, n-propyl and i-propyl are exemplified.

For the "substituent" in "phenyl group, naphthyl group, benzoyl group or 5-membered or 6-membered heteroring and its benzene-condensed ring, which may have one or more substituents", hydrogen atom, halogen, lower alkyl group, hydroxyl group, lower alkoxy group, nitro group, amino group (said amino group may be substituted with lower alkyl group, lower alkanoyl group or benzoyl group), phenyl group( this phenyl group may be substituted with halogen, lower alkyl group or lower alkoxy group), lower alkanoyloxy group, carboxyl group, methylenedioxy group, sulfamoyl group (this sulfamoyl group may be substituted with lower alkyl group), trifluoromethyl group, or the like can be mentioned. For "halogen", fluorine, chlorine, bromine and iodine are exemplified.

For "lower alkoxy", straight chain or branched ones with carbon atoms of 1 to 6 such as methoxy, ethoxy, n-propoxy and i-propoxy are exemplified. For "lower alkanoyl", ones with carbon atoms of 1 to 4 such as acetyl and propionyl are exemplified. For "lower alkanoyloxy", ones with carbon atoms of 1 to 4 such as acetyloxy and propionyloxy are exemplified.

The "5-membered or 6-membered heterocycle and its benzene-condensed ring" mean saturated or unsaturated monocyclic or polycyclic heterocyclic groups capable of containing one or more nitrogen, oxygen and sulfur atoms and, piperidyl, piperazinyl, furyl, thienyl, imidazolyl, thiazolyl, pyridyl, benzofuryl, benzothienyl, indolyl, quinazolyl, etc. can be exepmlified.

"Lower alkylene" means ones with carbon atoms of 1 to 6 and methylene, ethylene, trimethylene, etc. are exemplified. "Lower alkenylene" applied similarly to "lower alkylene" but has carbon atoms of 2 to 6 and unsaturated bond(s).

The "eliminating group" is halogen, lower alkoxy or hydroxy and preferable one is halogen. "Their salts" mean salts admissible as drugs and, for example, salts with cations such as sodium and potassium or with inorganic acids (hydrochloric acid, sulfuric acid, etc.) or organic acids (p-toluenesulfonic acid etc.) can be included.

The compounds of the present invention can be prepared through processes shown below.

(A) Compounds represented by the general formula (1) can be obtained by reacting compounds represented by a general formula (3)

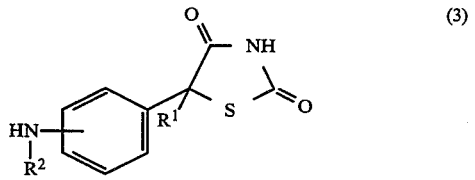

[wherein $R^1$ and $R^2$ are same as above], with compounds represented by a general formula (4)

[wherein $R^3$, A, Z and B are same as above], in the presence of suitable base or condensing agent.

This reaction can be conducted beneficially in a solvent such as dioxane, dimethylformamide or ethyl acetate in the presence of alkali metal hydride such as sodium hydride, for example, alkali metal hydroxide such as sodium hydroxide, for example , alkali metal carbonate such as potassium carbonate, for example, or organic base such as pyridine or triethylamine, for example, as a base.

For the condensing agents, for example, dicyclohexylcarbodiimide, diethylphosphoryl cyanide, etc. are exemplified. The reaction temperature is within a range from 0° to 120 ° C. and the reaction completes for 1 to 5 hours.

(B) Compounds represented by the general formula (2) can be obtained by condensing compounds represented by a general formula (3a)

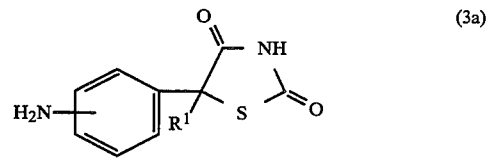

[wherein $R^1$ is same as above], or their salts with compounds represented by a general formula (5)

[wherein $R^3$ and $R^4$ are same as above].

This reaction can be conducted in a solvent inert to reaction such as ethanol, toluene or xylene, for example, in the presence of, for example, p-toluenesulfonic acid or the like as a catalyst or in the absence of catalyst. The reaction is conducted within a range from room temperature to boiling point of solvent and the reaction completes for 1 to 5 hours.

(C) Among compounds represented by the general formula (1), such compounds that $R^2$ is hydrogen atom, A is bonding hand and B is lower alkylene can also be obtained by reducing compounds represented by the general formula (2). This reaction can be conducted in a solvent inert to reaction such as methanol, ethanol, ether or tetrahydrofuran, for example in the presence of, for example, sodium borohydride, lithium aluminum hydride or the like as a reducing agent. The reaction is conducted within a range from 0° C. to boiling point of solvent and the reaction completes for 1 to 5 hours.

The compounds obtainable through said processes can be isolated and purified by publicly known separation and purification means, for example, solvent extraction, recrystallization, chromatography, etc.

If pharmaceutically admissible salts of compounds represented by the general formula (1) or general formula (2) are further needed, they can be obtained by reacting with cation-copossessing bases such as sodium hydroxide and potassium hydroxide, for example, inorganic acids such as hydrochloric acid and sulfuric acid, for example, and organic acids such as fumaric acid and oxalic acid, for example.

Moreover, because the inventive compounds represented by the general formula (1) and general formula (2) have one or more asymmetric carbon atoms, these exist optical isomers, but the invention also includes those optical isomers and racemic modifications. Embodiment to put the invention into practice The preparative examples and examples of the inventive compounds will be described to illustrate the invention in more detail.

EXAMPLE 1

5-(4-Benzoylaminophenyl)thiazolidine-2,4-dione

Into 20 ml of dioxane were dissolved 0.5 g of 5-(4-aminophenyl) thiazolidine-2,4-dione, and, after added 0.34 g of benzoyl chloride and further added dropwise 0.24 g of triethylamine, the mixture was refluxed for 1 hour. After cooling by standing, the reaction mixture was poured into 150 ml of ice water and the crystals deposited were collected by filtration, washed with water and dried. These were recrystallized from chloroform to obtain 0.70 g of title compound.

m.p. 240.0°–245.0° C.
Elemental analysis (%) As $C_{16}H_{12}N_2O_3S$
Calculated C 61.53 H 3.87 N 8.97
Observed C 61.65 H 3.88 N 8.75

EXAMPLE 2

5-(4-Piperonyloylaminophenyl)thiazolidine-2,4-dione

Into 20 ml of dimethylformamide were dissolved 1.00 g of 5-(4-aminophenyl)thiazolidine-2,4-dione and 0.80 g of piperonylic acid, and, after added 1.12 g of diethylphosphoryl cyanide and then 0.50 g of triethylamine at 0° C., the mixture was stirred for 1 hour as it was. Thereafter, the reaction mixture was brought to room temperature and stirred for 2 hours. Then, it was poured into 200 ml of water and, after made acidic with hydrochloric acid, the crystals deposited were collected by filtration. These were recrystallized from ethanol to obtain 1.05 g of title compound.

m.p. 275.0°–277.0° C.
Elemental analysis (%) As $C_{17}H_{12}N_2O_5S$
Calculated C 57.30 H 3.39 N 7.86
Observed C 57.39 H 3.28 N 7.81

EXAMPLE 3

5-(4-(p-Toluenesulfonylamino)phenyl)thiazolidine-2,4-dione

Into 10 ml of pyridine were dissolved 0.50 g of 5-(4-amino-phenyl) thiazolidine-2,4-dione, and after added 0.46 g of p-toluenesulfonyl chloride, the mixture was stirred for 1 hour at room temperature. After the completion of reaction, the reaction mixture was poured into ice water, which was extracted with ethyl acetate. The organic layer was washed with 10% hydrochloric acid, washed with water and dried. Then, solvent was distilled off. The residue was recrystallized from benzene to obtain 0.65 g of title compound.

m.p. 215.0°–218.0° C.
Elemental analysis (%) As $C_{16}H_{14}N_2O_4S_2$:
Calculated C; 53.02, H; 3.89, N 7.73,
Observed C;53.29, H; 3.86, N 7.75.

EXAMPLE 4 THROUGH 51

By the similar methods to Example 1 through 3, following compounds were obtained.

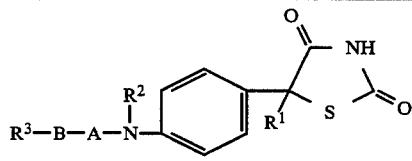

| Example | R³—B—A— | R¹ | R² | Melting point (°C.) | Solvent for recrystallization | Elemental analysis (%) Calculated observed |
| --- | --- | --- | --- | --- | --- | --- |
| 4 | O₂N—⟨⟩—CO— | H | H | 214~215 | CH₃CN | $C_{16}H_{11}N_3O_5S$<br>C: 53.78 H: 3.10 N: 11.76<br>53.74   3.05   11.78 |
| 5 | Br—⟨⟩—CO— | H | H | 266~269 | Dioxane | $C_{16}H_{11}BrN_2O_3S$<br>C: 49.12 H: 2.83 N: 7.16<br>49.20   2.92   6.88 |
| 6 | Cl—⟨⟩—CO— | H | H | 245~250 | CHCl₃ | $C_{16}H_{11}ClN_2O_3S$<br>C: 55.42 H: 3.20 N: 8.08<br>55.19   3.15   7.78 |
| 7 | H₃CO—⟨⟩—CO— | H | H | 234~235 | CHCl₃ | $C_{17}H_{14}N_2O_4S$<br>C: 59.64 H: 4.12 N: 8.18<br>59.30   4.07   7.98 |
| 8 | F—⟨⟩—CO— | H | H | 239~241 | CHCl₃ | $C_{16}H_{11}FN_2O_3S$<br>C: 58.18 H: 3.36 N: 8.48<br>58.24   3.42   8.28 |
| 9 | CH₃—⟨⟩—CO— | H | H | 245~250 | CHCl₃ | $C_{17}H_{14}N_2O_3S$<br>C: 62.56 H: 4.32 N: 8.58<br>62.35   4.34   8.47 |

-continued

| No. | Structure | | | mp (°C) | Solvent | Formula / Analysis |
|---|---|---|---|---|---|---|
| 10 | biphenyl-CO— | H | H | 286~289 | CHCl₃ | $C_{22}H_{16}N_2O_3S \cdot 1/5H_2O$<br>C: 67.40 H: 4.22 N: 7.16<br>  67.49   4.22   7.08 |
| 11 | (CH₃)₂N–C₆H₄–CO— | H | H | 275~278 | Dioxane | $C_{18}H_{17}N_3O_3S$<br>C: 60.83 H: 4.82 N: 11.82<br>  60.60   4.83  11.64 |
| 12 | CF₃–C₆H₄–CO— | H | H | 275~276 | CHCl₃ | $C_{17}H_{11}F_3N_2O_3S$<br>C: 53.68 H: 2.92 N: 7.37<br>  53.37   2.84   7.40 |
| 13 | (CH₃)₃C–C₆H₄–CO— | H | H | 272~275 | CHCl₃ | $C_{20}H_{20}N_2O_3S \cdot 1/6H_2O$<br>C: 64.66 H: 5.52 N: 7.54<br>  64.54   5.43   7.45 |
| 14 | H₃CCO₂–C₆H₄–CO— | H | H | 268~270 | Dioxane | $C_{18}H_{14}N_2O_5S$<br>C: 58.37 H: 3.81 N: 7.57<br>  58.39   3.76   7.47 |
| 15 | HO–(di-t-Bu)C₆H₂–CO— | H | H | 206~208 | Et₂O | $C_{24}H_{28}N_2O_4S \cdot 1/5H_2O$<br>C: 64.90 H: 6.44 N: 6.31<br>  64.72   6.26   6.30 |
| 16 | 2-OCH₃–C₆H₄–CO— | H | H | 193~195 | CHCl₃ | $C_{17}H_{14}N_2O_4S$<br>C: 59.64 H: 4.12 N: 8.18<br>  59.58   4.08   8.16 |
| 17 | 3-O₂N–C₆H₄–CO— | H | H | 244~246 | Dioxane-n-hexane | $C_{16}H_{11}N_3O_5S$<br>C: 53.78 H: 3.10 N: 11.76<br>  53.77   3.06  11.69 |
| 18 | 2-CH₃–C₆H₄–CO— | H | H | 211~213 | EtOH-n-hexane | $C_{17}H_{14}N_2O_3S$<br>C: 62.56 H: 4.32 N: 8.58<br>  62.94   4.24   8.24 |
| 19 | 2-NO₂–C₆H₄–CO— | H | H | 229~231 | EtOH-n-hexane | $C_{16}H_{11}N_3O_5S$<br>C: 53.78 H: 3.10 N: 11.76<br>  53.94   3.03  11.42 |
| 20 | 2-Cl–C₆H₄–CO— | H | H | 228~230 | CH₃CN | $C_{16}H_{11}ClN_2O_3S$<br>C: 55.42 H: 3.20 N: 8.08<br>  55.32   3.05   8.08 |
| 21 | 2-F–C₆H₄–CO— | H | H | 247~248 | CH₃CN | $C_{16}H_{11}FN_2O_3S$<br>C: 58.18 H: 3.36 N: 8.48<br>  58.10   3.28   8.57 |

-continued

| # | Structure | | | mp (°C) | Solvent | Formula / Analysis |
|---|---|---|---|---|---|---|
| 22 | 2-OCOCH₃-C₆H₄-CO- | H | H | 220~222 | EtOH-n-hexane | $C_{18}H_{14}N_2O_5S$<br>C: 58.37 H: 3.81 N: 7.56<br>58.54  3.90  7.43 |
| 23 | 2,4-Cl₂-C₆H₃-CO- | H | H | 240~242 | CHCl₃ | $C_{16}H_{10}Cl_2N_2O_3S$<br>C: 50.41 H: 2.64 N: 7.35<br>50.22  2.50  7.37 |
| 24 | 3,4-Cl₂-C₆H₃-CO- | H | H | 256~258 | Dioxane-n-hexane | $C_{16}H_{10}Cl_2N_2O_3S$<br>C: 50.41 H: 2.64 N: 7.35<br>50.44  2.56  7.48 |
| 25 | 3,4-(H₃CO)₂-C₆H₃-CO- | H | H | 274~275 | Dioxane-n-hexane | $C_{18}H_{16}N_2O_5S$<br>C: 58.06 H: 4.33 N: 7.52<br>58.07  4.33  7.39 |
| 26 | 4-H₃CO-C₆H₄-CO- | CH₃ | H | 179~180 | EtOH | $C_{18}H_{16}N_2O_4S$<br>C: 60.66 H: 4.52 N: 7.86<br>60.91  4.50  7.45 |
| 27 | 2,4-Cl₂-C₆H₃-CO- | CH₃ | H | 209~210.5 | EtOH | $C_{17}H_{12}Cl_2N_2O_3S$<br>C: 51.66 H: 3.06 N: 7.09<br>51.78  3.00  7.02 |
| 28 | 1-naphthyl-CO- | H | H | 229~231 | CH₃CN | $C_{20}H_{14}N_2O_3S$<br>C: 66.28 H: 3.89 N: 7.73<br>66.13  3.84  7.75 |
| 29 | 2-naphthyl-CO- | H | H | 265~267 | Dioxane | $C_{20}H_{14}N_2O_3S$<br>C: 66.28 H: 3.89 N: 7.73<br>66.02  3.80  7.65 |
| 30 | C₆H₅-CH₂CO- | H | H | 165~167 | CHCl₃ | $C_{17}H_{14}N_2O_3S$<br>C: 62.56 H: 4.32 N: 8.58<br>62.49  4.30  8.53 |
| 31 | 2,4-Cl₂-C₆H₃-CO- | H | CH₂CH₃ | 84~86<br>(Foamy crystal) | Column chromat. | Mass 408 (M⁺) |
| 32 | 4-HO-C₆H₄-CO- | H | H | 289~290 | EtOH-n-hexane | $C_{16}H_{11}N_2O_4S$<br>C: 58.71 H: 3.39 N: 8.56<br>58.48  3.61  8.31 |
| 33 | 4-(CH₃)₂NSO₂-C₆H₄-CO- | H | H | 201~203 | AcOEt-n-hexane | $C_{18}H_{17}N_3O_5S_2$<br>C: 51.54 H: 4.08 N: 10.02<br>51.93  4.15  9.95 |

-continued

| No. | Structure | | | m.p. (°C) | Solvent | Formula / Analysis |
|---|---|---|---|---|---|---|
| 34 | HO₂C—⟨C₆H₄⟩—SO₂— | H | H | 273~274 | EtOH-n-hexane | $C_{16}H_{12}N_2O_6S_2$<br>C: 48.97 H: 3.13 N: 7.07<br>49.30    3.23    7.07 |
| 35 | 2-pyridyl-CO— | H | H | 263~266 | CHCl₃ | $C_{15}H_{11}N_3O_3S$<br>C: 57.50 H: 3.54 N: 13.41<br>57.19    3.56    13.12 |
| 36 | 2-furyl-CO— | H | H | 264~266 | CHCl₃ | $C_{14}H_{10}N_2O_4S$<br>C: 55.62 H: 3.33 N: 9.27<br>55.37    3.31    9.09 |
| 37 | 2-thienyl-CO— | H | H | 253~255 | Dioxane | $C_{14}H_{10}N_2O_3S_2$<br>C: 52.84 H: 3.17 N: 8.80<br>52.69    3.08    8.71 |
| 38 | 2,5,7,8-tetramethyl-6-hydroxy-chroman-2-yl-CO— | H | H | 222~223 | CH₂Cl₂ | $C_{23}H_{24}N_2O_5S$<br>C: 62.71 H: 5.49 N: 6.36<br>62.29    5.37    6.31 |
| 39 | 2-(HO₂C)C₆H₄—CO— | H | H | 211.5~212 | EtOH | $C_{17}H_{12}N_2O_5S$<br>C: 57.30 H: 3.39 N: 7.86<br>57.25    3.29    7.67 |
| 40 | C₆H₅—CH=CH—CO— | H | H | 226~228 | EtOH | $C_{18}H_{14}N_2O_3S$<br>C: 63.89 H: 4.17 N: 8.28<br>64.01    4.22    8.27 |
| 41 | 3,4-Cl₂C₆H₃—CH₂CO— | H | H | 226~228 | EtOH | $C_{17}H_{14}Cl_2N_4O_3S$<br>C: 51.66 H: 3.06 N: 7.09<br>51.62    2.95    7.09 |
| 42 | 3-pyridyl-CH₂CO— | H | H | 245~250 | DMF—H₂O | $C_{16}H_{13}N_3O_3S\cdot1/5H_2O$<br>C: 58.06 H: 4.01 N: 12.69<br>58.06    3.94    12.76 |
| 43 | 4-EtO-C₆H₄—CO— | H | H | 279~282 | DMF—H₂O | $C_{18}H_{16}N_2O_4S\cdot1/5H_2O$<br>C: 60.05 H: 4.53 N: 7.78<br>60.19    4.57    7.90 |
| 44 | 2-OCH₃-4-Cl-C₆H₃—CO— | H | H | 214~215 | AcOEt | $C_{17}H_{13}ClN_2O_4S$<br>C: 54.19 H: 3.48 N: 7.43<br>54.13    3.40    7.35 |
| 45 | 2,4-di-OCH₃-C₆H₃—CO— | H | H | 245~249 | MeOH | $C_{18}H_{16}N_2O_5S$<br>C: 58.06 H: 4.33 N: 7.52<br>58.05    4.38    7.50 |

| 46 | 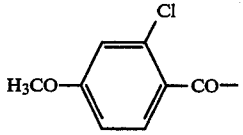 | H | H | 215~217 | AcOEt | C$_{17}$H$_{13}$ClN$_2$O$_4$S<br>C: 54.19 H: 3.48 N: 7.43<br>54.18    3.44    7.39 |

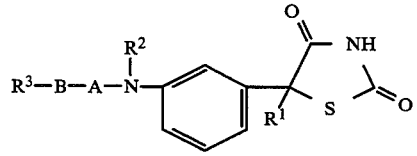

| Example | R$^3$—B—A— | R$^1$ | R$^2$ | Melting point (°C.) | Solvent for recrystallization | Elemental analysis (%)  Calculated  observed |
|---|---|---|---|---|---|---|
| 47 |  | H | H | 191~192 | EtOH | C$_{17}$H$_{14}$N$_2$O$_4$S<br>C: 59.64 H: 4.12 N: 8.18<br>59.92    4.11    8.10 |
| 48 | 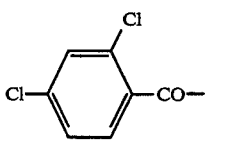 | H | H | 115~120<br>Foamy crystal | Column chromat. | Mass 380 (M$^+$) |
| 49 | 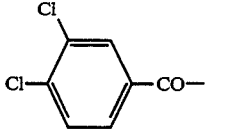 | H | H | 99~100<br>Foamy crystal | Column chromat. | Mass 380 (M$^+$) |
| 50 | 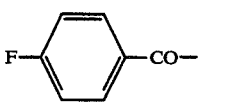 | H | H | 85~86<br>Foamy crystal | Column chromat. | Mass 330 (M$^+$) |
| 51 | 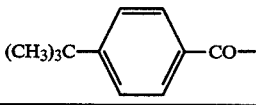 | H | H | 218~219 | AcOEt-n-hexane | C$_{20}$H$_{20}$N$_2$O$_3$S<br>C: 65.20 H: 5.47 N: 7.60<br>64.97    5.53    7.55 |

EXAMPLE 52

5-(4-(3,4-Dichlorobenzylideneamino)phenyl)thiazolidine-2,4-dione

Into 20 ml of ethanol were suspended 0.50 g of 5-(4-aminophenyl)-thiazolidine-2,4-dione, and, after added 0.42 g of 3,4-dichlorobenzaldehyde thereto, the suspension was refluxed for 3 hours. After cooling by standing, the crystals deposited were collected by filtration. The crude crystals were recrystallized from ethanol to obtain 0.79 g of title compound.

m.p. 216.5°–218.0° C.

Elemental analysis (%) As C$_{16}$H$_{10}$Cl$_2$N$_2$O$_2$S:
Calculated C; 52.62, H; 2.76, N 7.67.
Observed C; 52.58, H; 2.74, N 7.68.

EXAMPLE 53

5-(4-(3,4-Dichlorobenzylamino)phenyl)thiazolidine-2,4-dione

Into 40 ml of ethanol were suspended 0.40 g of 5-(4-(3,4-dichlorobenzylideneamino) phenyl)thiazolidine-2,4-dione, and, after added 0.24 g of sodium borohydride, the suspension was stirred for 2 hours at 50° C. The reaction mixture was poured into 200 ml of water, which was extracted with ethyl acetate. The organic layer was washed with water and dried. Then, solvent was distilled off. The residue was recrystallized from iso-propanol to obtain 0.20 g of title compound.

m.p. 132.0°–133.0° C.

Elemental analysis (%) As C$_{16}$H$_{12}$Cl$_2$N$_2$O$_2$S;
Calculated C, 52.32; H, 3.29; N, 7.63;
Observed C; 52.26, H; 3.28, N; 7.64.

EXAMPLE 54 THROUGH 62

By the similar methods to Example 52 and 53, following compounds were obtained.

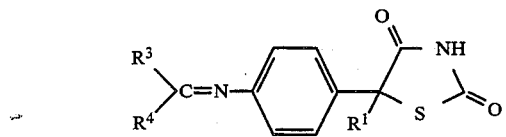

| Example | R³ | R⁴ | R¹ | Melting point (°C.) | Solvent for recrystallization | Elemental analysis (%) Calculated observed |
|---|---|---|---|---|---|---|
| 54 | 2,4-dichlorophenyl | H | H | 150~151 | CH₂Cl₂-n-hexane | $C_{16}H_{10}Cl_2N_2O_2S$<br>C: 52.62 H: 2.76 N: 7.67<br>   52.33   2.64   7.56 |
| 55 | 4-methoxyphenyl (H₃CO—C₆H₄—) | H | H | 200~202 | EtOH | $C_{17}H_{14}N_2O_3S$<br>C: 62.56 H: 4.32 N: 8.58<br>   62.47   4.30   8.49 |

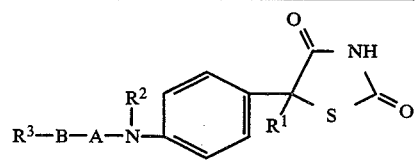

| Example | R³—B—A— | R¹ | R² | Melting point (°C.) | Solvent for recrystallization | Elemental analysis (%) Calculated observed |
|---|---|---|---|---|---|---|
| 56 | 2-pyridyl-CH₂— | H | H | 222~223 | AcOEt | $C_{15}H_{13}N_3O_2S \cdot \tfrac{1}{4}H_2O$<br>C: 59.29 H: 4.40 N: 13.82<br>   59.31   4.40   13.74 |
| 57 | 3-pyridyl-CH₂— | H | H | 178~180 | EtOH | $C_{15}H_{13}N_3O_2S$<br>C: 60.18 H: 4.38 N: 14.04<br>   59.92   4.37   13.96 |
| 58 | 4-pyridyl-CH₂— | H | H | 239~240 | MeOH | $C_{15}H_{13}N_3O_2S \cdot 1/5H_2O$<br>C: 59.47 H: 4.39 N: 13.87<br>   59.29   4.23   13.90 |
| 59 | phenyl-CH₂— | H | H | 181 | MeOH | $C_{16}H_{14}N_2O_2S$<br>C: 64.41 H: 4.73 N: 9.39<br>   64.34   4.64   9.39 |
| 60 | phenyl-CH₂CH₂— | H | H | 160~161 | MeOH | $C_{17}H_{16}N_2O_2S$<br>C: 65.36 H: 5.16 N: 8.97<br>   65.33   5.14   8.96 |
| 61 | 2,4-dichlorophenyl-CH₂— | H | H | 182~183 | AcOEt | $C_{16}H_{12}Cl_2N_2O_2S$<br>C: 52.33 H: 3.29 N: 7.63<br>   52.48   3.22   7.61 |
| 62 | 4-methoxyphenyl-CH₂— (H₃CO—C₆H₄—CH₂—) | H | H | 150~152 | CH₂Cl₂-n-hexane | $C_{17}H_{16}N_2O_3S \cdot 1/10H_2O$<br>C: 61.84 H: 4.94 N: 8.48<br>   61.72   4.86   8.44 |

Experiment 1

Enhancement of insulin sensitivity in rats

After rats were orally administered with the compound of Example 23 once daily for 5 days at 10 mg/kg/day, they were fasted for 18 hours and then insulin was intraperitoneally injected at 0.1 unit/kg. Blood samples were collected from the tail vein 0 and 1 hour after the injection of insulin for the determination of blood glucose (Table 1).

Experiment 2

Improvement of glucose tolerance in genetically obese mice

Genetically obese mice (CS57BL ob/ob mice) were orally administered with the compound of Example 23 once daily for 5 days at 10, 30 or 100 mg/kg/day, respectively. They were fasted for 18 hours and then 2 g/kg of glucose was orally administered. Blood samples were collected from the tail vein 0, 30, 60 and 120 minutes after the administration of glucose for the determination of blood glucose (Table 2).

From these results in Tables 1 and 2, it was shown that the compound of the present invention possessed potent blood glucose lowering action.

Experiment 3

Inhibition of aldose reductase in vitro

According to the method of Hyman and Kinoshita (J. Biol. Chem., 240, 877, 1965), inhibitory activity of the compound of Example 23 on aldose reductase extracted from rat lens was investigated. As a result, the following $IC_{50}$ value was obtained (Table 3).

Experiment 4

Inhibition on sorbitol accumulation in tissues of diabetic rats

After diabetic rats were prepared by injecting streptozotocin, they were orally administered with the compound of Example 23 once daily 2 weeks at 4, 16 or 64 mg/kg/day, respectively. The sorbitol content in nerve and retina was determined to calculate $ED_{50}$ value (Table 4).

From these results in Table 3 and 4, it was suggested that the compound of the present invention possessed potent inhibitory activity on aldose reductase.

TABLE 1

| Group | n | 0 hour value − 1 hour value (mg %) |
|---|---|---|
| Reference (insulin only) | 5 | 11.0 ± 0.8 |
| Example 23 10 mg/kg | 5 | 19.4 ± 1.5* |

*$P < 0.01$

TABLE 2

| | OGTT (% of control) | | |
|---|---|---|---|
| Compound | 10 mg/kg | 30 mg/kg | 100 mg/kg |
| Example 23 | 93.5 | 89.2 | 74.1 |

TABLE 3

| Compound | $IC_{50}$ value |
|---|---|
| Example 23 | $9 \times 10^{-8}$ M |

TABLE 4

| Compound | $ED_{50}$ value (mg/kg/day) | |
|---|---|---|
| | Nerve | Retina |
| Example 23 | 14.5 | 26.5 |

Utilizability in the industry

The novel thiazolidine-2,4-dione derivatives and their salts in accordance with the invention possess superior blood sugar-lowering action together with remarkable aldose reductase-inhibitory action, thus they are useful as the drugs for the therapy and prevention of diabetes and the complication thereof.

What is claimed is:

1. Thiazolidine-2,4-dione derivatives represented by formula (1)

$$R^3-B-A-N(R^2)-\text{[phenyl with }R^1\text{]}-\text{CH}-\text{C(=O)-NH-C(=O)-S (thiazolidine-2,4-dione)} \quad (1)$$

where $R^1$ and $R^2$ each independently represent hydrogen atoms or $C_{1-6}$ alkyl groups;

$R^3$ denotes a phenyl group, napthyl group, benzoyl group or saturated or unsaturated monocyclic or polycyclic heterocyclic group containing one or more nitrogen, oxygen or sulfur atoms, all of said $R^3$ groups being optionally substituted with one or more substituents selected form the group consisting of hydrogen, fluorine, chlorine, bromine, iodine, $C_{1-6}$ alkyl groups, hydroxyl, $C_{1-6}$ alkoxy groups, nitro, amino which itself may optionally be substituted with a $C_{1-6}$ alkyl group or a $C_{1-4}$ alkanoyl group or a benzoyl group, phenyl which itself may be substituted with fluorine or chlorine or bromine or iodine or a $C_{1-6}$ alkyl group or a $C_{1-6}$ alkoxy group, $C_{1-4}$ alkanoyloxy, carboxyl, methylenedioxy, sulfamoyl which may itself be substituted with a $C_{1-6}$ alkyl group, and trifluoromethyl;

A denotes a carbonyl group, a sulfonyl group or a single bond; and

B denotes a $C_{1-6}$ alkylene, $C_{2-6}$ alkenylene or a single bond; and salts thereof.

2. The thiazolidine-2,4-dione derivatives as claimed in claim 1, wherein $R^3$ is a saturated or unsaturated monocyclic or polycyclic heterocyclic group containing one or more nitrogen, oxygen or sulfur atoms which is selected from the group consisting of piperidyl, piperazinyl, furyl, thienyl, imidazolyl, thiazolyl, pyridyl, benzofuryl, benzothienyl, indolyl and quinazolyl and which is optionally substituted.

3. The thiazolidine-2,4-dione derivatives as claimed in claim 1, wherein $R^3$ is an optionally substituted benzoyl group.

4. The thiazolidine-2,4-dione derivatives as claimed in claim 1, wherein $R^3$ is an optionally substituted naphthyl group.

5. The thiazolidine-2,4-dione derivatives as claimed in claim 1, wherein $R^3$ is an optionally substituted phenyl group.

6. The thiazolidine-2,4-dione derivatives as claimed in claim 1, wherein A is a carbonyl group.

7. The thiazolidine-2,4-dione derivatives as claimed in claim 1, wherein A is a sulfonyl group.

8. The thiazolidine-2,4-dione derivatives as claimed in claim 1, wherein B is a $C_{1-6}$ alkylene group.

9. The thiazolidine-2,4-dione derivatives as claimed in claim 1, wherein B is a $C_{2-6}$ alkenylene group.

10. The thiazolidine-2,4-dione derivatives as claimed in claim 8, wherein A is a single bond.

11. The thiazolidine-2,4-dione derivatives as claimed in claim 1, wherein B is a single bond.

12. The thiazolidine-2,4-dione derivatives as claimed in claim 1, wherein $R^1$ and $R^2$ are hydrogen and where $R^3$-B-A- is selected from the group consisting of

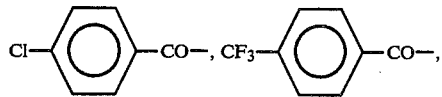

-continued

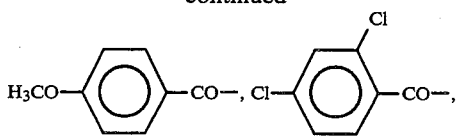

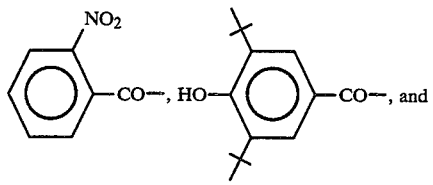

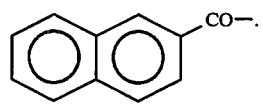

13. A blood sugar-lowering agent comprising at least one of the thiazolidine-2,4-dione derivatives claimed in claim 1.

14. An aldose reductase-inhibitory agent comprising at least one of the thiazolidine-2,4-dione derivatives claimed in claim 1.

* * * * *